United States Patent
Sylvestre et al.

(10) Patent No.: US 12,288,623 B2
(45) Date of Patent: Apr. 29, 2025

(54) METHOD AND SYSTEM FOR IDENTIFYING SUBJECTS WHO ARE POTENTIALLY IMPACTED BY A MEDICAL CONDITION

(71) Applicants: OPTINA DIAGNOSTICS, INC., Montreal (CA); Jean Philippe Sylvestre, Kirkland (CA); Claudia Chevrefils, Saint-Laurent (CA); David Lapointe, Pointe-Claire (CA)

(72) Inventors: Jean Philippe Sylvestre, Kirkland (CA); David Lapointe, Pointe-Claire (CA); Claudia Chevrefils, Saint-Laurent (CA)

(73) Assignee: OPTINA DIAGNOSTICS, INC., Montreal (CA)

( * ) Notice: Subject to any disclaimer, the term of this patent is extended or adjusted under 35 U.S.C. 154(b) by 329 days.

(21) Appl. No.: 17/440,274

(22) PCT Filed: Mar. 16, 2020

(86) PCT No.: PCT/IB2020/052394
§ 371 (c)(1),
(2) Date: Sep. 17, 2021

(87) PCT Pub. No.: WO2020/188471
PCT Pub. Date: Sep. 24, 2020

(65) Prior Publication Data
US 2022/0157470 A1 May 19, 2022

Related U.S. Application Data

(60) Provisional application No. 62/820,587, filed on Mar. 19, 2019.

(51) Int. Cl.
*G16H 50/70* (2018.01)
*A61B 3/00* (2006.01)
(Continued)

(52) U.S. Cl.
CPC .......... *G16H 50/70* (2018.01); *A61B 3/0025* (2013.01); *A61B 3/145* (2013.01); *A61B 5/4848* (2013.01);
(Continued)

(58) Field of Classification Search
CPC ........ G16H 50/70; G16H 30/40; G16H 10/60; G16H 10/20; G16H 50/20; A61B 3/0025;
(Continued)

(56) References Cited

U.S. PATENT DOCUMENTS

| | | | |
|---|---|---|---|
| 6,988,995 B2 | 1/2006 | Zhou et al. | |
| 7,905,417 B2 | 3/2011 | Leiper | |

(Continued)

FOREIGN PATENT DOCUMENTS

| | | |
|---|---|---|
| EP | 2356579 B1 | 5/2015 |
| JP | 2007507814 A | 3/2007 |

(Continued)

OTHER PUBLICATIONS

Solomon et al., European Prevention of Alzheimer's Dementia Longitudinal Cohort Study, Oct. 10, 2018, BMJ Open, pp. 1-12. (Year: 2018).*

(Continued)

*Primary Examiner* — Christopher L Gilligan
(74) *Attorney, Agent, or Firm* — BCF LLP

(57) ABSTRACT

Subjects who are potentially impacted by a medical condition are identified. An experimental group includes subjects having a positive indication for a specific criterion related to the medical condition in their medical profiles. A control groups includes subjects having a negative indication for the specific criterion. An artificial intelligence system is trained using the specific criterion and secondary characteristics of the subjects of the experimental and control groups to construct a classifier for the medical condition. The classifier (Continued)

is used to extract a target group of subjects from a population of subjects. A medical profile of each subject of the target group is marked as potentially affected by the medical condition. A system includes the artificial intelligence system and a database for storing the medical profiles. Deep learning or machine learning may be used to analyze medical images such as retinal images.

20 Claims, 9 Drawing Sheets

(51) Int. Cl.
    *A61B 3/14*     (2006.01)
    *A61B 5/00*     (2006.01)
    *G16H 30/40*     (2018.01)

(52) U.S. Cl.
    CPC .......... *A61B 5/7267* (2013.01); *A61B 5/7275* (2013.01); *G16H 30/40* (2018.01)

(58) Field of Classification Search
    CPC ..... A61B 3/145; A61B 5/4848; A61B 5/7267; A61B 5/7275; A61B 3/12; A61B 5/0033; A61B 5/14546; A61B 5/4842; G06N 20/00
    See application file for complete search history.

(56) References Cited

U.S. PATENT DOCUMENTS

| | | | |
|---|---|---|---|
| 8,756,076 | B2 | 6/2014 | Griffin et al. |
| 9,008,391 | B1 | 4/2015 | Solanki et al. |
| 9,245,337 | B2 | 1/2016 | Schmidt et al. |
| 2007/0055552 | A1 | 3/2007 | St. Clair et al. |
| 2007/0130206 | A1 | 6/2007 | Zhou et al. |
| 2009/0030290 | A1 | 1/2009 | Kozuch et al. |
| 2009/0062623 | A1 | 3/2009 | Cohen et al. |
| 2011/0282688 | A1 | 11/2011 | Raggousis |
| 2012/0084092 | A1 | 4/2012 | Kozuch et al. |
| 2012/0203086 | A1 | 8/2012 | Rorabaugh et al. |
| 2013/0246085 | A1 | 9/2013 | Seddiqui et al. |
| 2015/0104087 | A1* | 4/2015 | Katuwal ................... G06T 7/11 382/128 |
| 2015/0218640 | A1 | 8/2015 | Brandon et al. |
| 2016/0092721 | A1 | 3/2016 | Kanagasingam et al. |
| 2018/0038839 | A1 | 2/2018 | Probert et al. |
| 2018/0068083 | A1 | 3/2018 | Cohen et al. |
| 2018/0204327 | A1 | 7/2018 | Matthews et al. |
| 2020/0375521 | A1* | 12/2020 | Hadoux .............. G06V 10/143 |
| 2021/0193320 | A1* | 6/2021 | Shukla .................... G06F 16/27 |
| 2021/0236053 | A1* | 8/2021 | Narayan ............. A61B 5/4836 |
| 2022/0005605 | A1* | 1/2022 | Tuytten .................. G16H 50/30 |

FOREIGN PATENT DOCUMENTS

| | | | | |
|---|---|---|---|---|
| JP | | 2013545516 A | 12/2013 | |
| WO | | 2005036446 A2 | 4/2005 | |
| WO | | 2008124138 A1 | 10/2008 | |
| WO | | 2011039515 A1 | 4/2011 | |
| WO | | 2012061078 A2 | 5/2012 | |
| WO | WO-2012074565 A1 * | | 6/2012 | ............ A61K 45/00 |
| WO | | 2016041062 A1 | 3/2016 | |
| WO | | 2016094330 A2 | 6/2016 | |
| WO | | 2018073784 A1 | 4/2018 | |
| WO | | 2018200840 A1 | 11/2018 | |

OTHER PUBLICATIONS

Akkara et al., "Role of artificial intelligence and machine learning in ophtalmology", Kerala Journal of Ophthalmology, Jan. 1, 2019, p. 150-160.

Bernardes et al., "Retinal Biomarkers of Alzheimer's Disease: Insights from Transgenic Mouse Models", Jun. 2, 2017, Springer International Publishing AG 2017, pp. 541-550.

Suplementary European Search Report issued by the EPO on Nov. 9, 2022 in connection with the European corresponding application No. 20773168.8.

Miotto et al., "Deep Leraning for Healthcare: Review, Opportunities and Challenges", May 6, 2017, Briefings in Bioinformatics, 2018, pp. 1236-1246.

Corrected version of International Search Report and Written Opinion of PCT/IB2020/052394; ISA/CA; Jun. 29, 2020; Veeresh Nadarajan.

Office Action issued by the Japanese Patent Office (JPO) in connection with Japanese patent application No. 2021-559470 on Apr. 22, 2024, 12 pages (EN translation).

Examiner's Report issued by the Canadian Intellectual Property Office (CIPO) on Mar. 11, 2025 in connection with Canadian patent application No. 3,134,081, 12 pages.

\* cited by examiner

METHOD AND SYSTEM FOR IDENTIFYING SUBJECTS WHO ARE POTENTIALLY IMPACTED BY A MEDICAL CONDITION

CROSS-REFERENCE

The present application claims priority from U.S. Provisional Patent Application Ser. No. 62/820,587, filed on Mar. 19, 2019, the entirety of which is incorporated by reference herein.

TECHNICAL FIELD

The present disclosure relates to the field of medical information. More specifically, the present disclosure relates to a method and a system for identifying subjects who are potentially impacted by a medical condition.

BACKGROUND

Doctors and other practitioners in the medical field collect and analyze medical information, for example results of tests provided by use of medical device or results of laboratory tests, to establish diagnoses for their patients. Traditionally, medical information was stored on paper at the clinician's office; there was a great concern that computerized medicine would lead to information theft and to dissemination of sensitive personal information.

In recent years, medical information has increasingly been stored on computers and communicated over networks. Although the accuracy and the availability of medical information have improved, progress has been quite limited in the computerized analysis of medical information. A wealth of data about the medical history of patients is still underutilized.

Therefore, there is a need for new techniques for analysis medical information acquired for a population of subjects.

SUMMARY

According to the present disclosure, there is provided a method for identifying subjects who are potentially impacted by a medical condition. An experimental group is defined in a database containing medical profiles for a population of subjects. The experimental group includes one or more subjects having a positive indication for a specific criterion related to the medical condition in their medical profiles. A control group is also defined in the database. The control group includes one or more subjects having a negative indication for the specific criterion related to the medical condition in their medical profiles. An artificial intelligence system is trained using the specific criterion and information related to one or more secondary characteristics of the subjects of the experimental and control groups to construct a classifier for the medical condition. The classifier is used to extract, from the population of subjects in the database, a target group including one or more subjects. In the database, a medical profile of each subject of the target group of subjects is marked as potentially affected by the medical condition.

According to the present disclosure, there is also provided a method for evaluating a potentiality of subjects for being affected by a medical condition. An experimental group is defined in a database containing medical profiles for a population of subjects. The experimental group includes one or more subjects having a positive indication for a specific criterion related to the medical condition in their medical profiles. A control group is also defined in the database. The control group includes one or more subjects having a negative indication for the specific criterion related to the medical condition in their medical profiles. An artificial intelligence system is trained using the specific criterion and information related to one or more secondary characteristics of the subjects of the experimental and control groups to construct a classifier for the medical condition. The classifier is used to evaluate a potential of being affected by the medical condition for a given subject. The evaluated potential of being affected by the medical condition is stored in the database in a medical profile of the given subject.

According to the present disclosure, there is also provided a system for identifying subjects who are potentially impacted by a medical condition. The system comprises a database, a communication interface, a processor and a non-transitory computer-readable medium. The database is adapted for storing medical profiles for a population of subjects. The communication interface is adapted for receiving, from a first medical modality, positive and negative indications for a specific criterion related to the medical condition for a subset of the population of subjects, and for receiving, from one or more second medical modalities, information related to one or more secondary characteristics for the population of subjects. The processor is operatively connected to the database and to the communication interface. The non-transitory computer-readable medium has stored thereon machine executable instructions for performing, when executed by the processor, the method for identifying subjects who are potentially impacted by a medical condition.

According to the present disclosure, there is also provided a system for identifying subjects who are potentially impacted by a medical condition. The system comprises a database, a communication interface, an artificial intelligence system, and a controller. The database is adapted for storing medical profiles for a population of subjects. The communication interface is adapted for receiving, from a first medical modality, positive and negative indications for a specific criterion related to the medical condition for a subset of the population of subjects, and for receiving, from one or more second medical modalities, one or more secondary characteristics for the population of subjects. The artificial intelligence system is configured to construct a classifier for the medical condition based on a provided criterion and on provided information related to secondary characteristics. The artificial intelligence system is also configured to use the classifier to extract, from the population of subjects in the database, a target group including one or more subjects. The controller is operatively connected to the database, to the communication interface and to the artificial intelligence system. The controller is configured to define, in the database, an experimental group including one or more subjects having the positive indication for the specific criterion in their medical profiles, define, in the database, a control group including one or more subjects having the negative indication for the specific criterion in their medical profiles, provide the specific criterion and the information related to the one or more secondary characteristics of the subjects of the experimental and control groups to the artificial intelligence system, receive identifications of the subjects of the target group from the artificial intelligence system, and mark, in the database, the medical profile of each subject of the target group of subjects as potentially affected by the medical condition.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various drawings.

DETAILED DESCRIPTION

Figure 1:
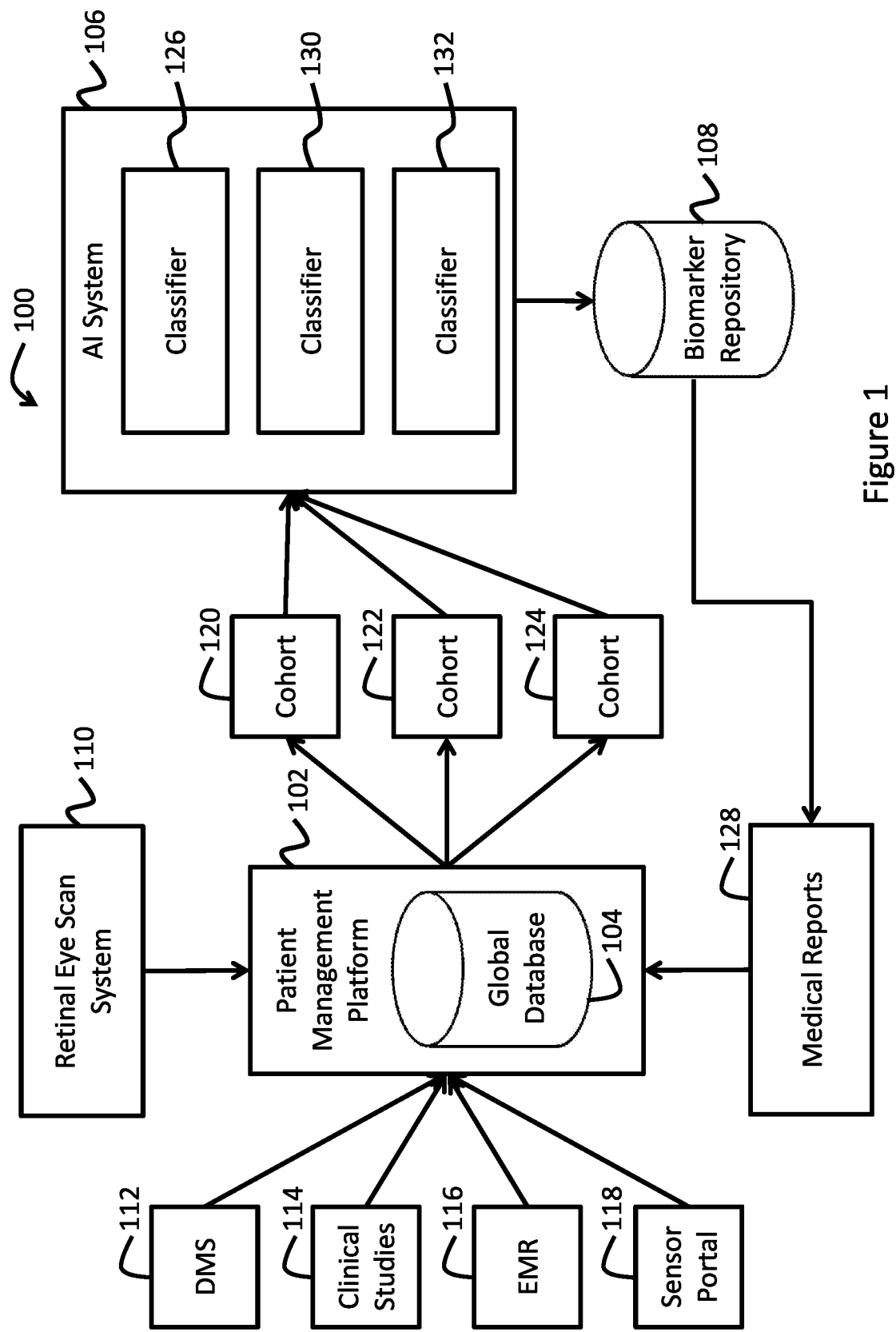
FIG. 1 is a general architecture diagram of a network adapted to acquire and process medical information according to an embodiment.

Various aspects of the present disclosure generally address one or more of the problems related to the under-utilization of medical information related to subjects in the general population.

Generally stated, the present disclosure introduces a technology in which an artificial intelligence (AI) system is trained to construct a classifier using information obtained by direct observation of a specific criterion related to a medical condition of a number of test subjects. The classifier is then applied to medical profiles of a general population of subjects to identify a target group of subjects who are potentially affected by the same medical condition. This direct observation of the specific criterion provides so-called "ground truth" contents, or "gold standard", for reliably training the AI system.

In addition to the specific criterion, information related to at least one secondary characteristic of test subjects is also used to train the AI system for constructing the classifier.

An example of a positive indication that a specific criterion has been directly observed in a given subject may comprise a direct detection of a specific biomarker in the given subject. The classifier may then be constructed to identify the subjects of the target group based on a likelihood of the presence of the specific biomarker in the subjects of the target group. A non-limiting and illustrative example of the present technology concerns the identification of a target group of subjects who are potentially affected by Alzheimer's disease (AD). AD may be diagnosed in a given test subject via direct observation, using a positron emission tomography (PET) scan to detect and quantify the presence of amyloid in the subject's brain, amyloid being a specific biomarker associated to AD. In one embodiment, when amyloid is detected in the given test subject's brain, the specific criterion—the presence of amyloid—is said to be positive. In this embodiment, the specific criterion is negative for the given test subject if amyloid is not detected in the given test subject's brain. In another embodiment, an amount of amyloid may be quantified based on the PET scan result and the positive indication may be provided if the quantity of amyloid exceeds a predetermined threshold, the indication being negative if the quantity of amyloid is less than the predetermined threshold. Whether positive or negative, the result of a PET scan is considered reliable and thus forms a "ground truth" diagnosis for the given test subject.

Continuing with the same non-limiting and illustrative example, multispectral retinal scans are data rich images in which specific features invisible to the human eye can allow detection of certain health issues, including AD. Secondary characteristics that provide signs of AD in a subject may be revealed by analyzing features in the retina of the subject, this analysis providing evidence of the presence of amyloid in the brain of the subject. The anomaly may for example be detected by use of a texture analysis of the image of the retina. Relevant imaging techniques are described in International Patent Application Publication No. WO 2016/041062 A1 to Sylvestre et al., published on Mar. 23, 2016, and in International Patent Application Publication No. WO 2018/073784 A1 to Sylvestre et al., published on Apr. 26, 2018, the disclosures of which are incorporated by reference herein in their entirety.

In the above example, test subjects receiving a positive value for the specific criterion that amyloid is detected by a PET scan of their brains are placed in an experimental group, which is a subset of the general population. Other test subjects receiving a negative value for the specific criterion, amyloid not being detected by a PET scan of their brains, are placed in a control group, which is another subset of the general population. Imaging of the retinas of the subjects of the experimental and control groups are obtained and are processed to define secondary characteristics of these subjects. These information elements are used to train the AI system. Without being absolutely true in all cases, the members of the experimental groups, in which amyloid has been positively detected, will generally show a specific texture in their retinas. Conversely, the members of the control groups, in which amyloid has not detected, will generally not show such specific texture in their retinas. The classifier constructed by the trained AI system will then be able to classify other subjects of the general population as being part, or not, of a target group of subjects being potentially affected by Alzheimer's disease based on the texture of their retinas. Table I summarizes results for a very small, illustrative population of subjects.

TABLE I

| Subject ID | Specific Criterion | Secondary Characteristic | Group |
| --- | --- | --- | --- |
| A | Amyloid positive in PET scan | Specific texture correlating to amyloid in the brain | Experimental |
| B | Amyloid negative in PET scan | No specific texture | Control |
| C | Not available | No specific texture | None |
| D | Not available | Specific texture correlating to amyloid in the brain | Target |

TABLE I-continued

| Subject ID | Specific Criterion | Secondary Characteristic | Group |
|---|---|---|---|
| E | Not available | Specific texture correlating to amyloid in the brain | Target |
| F | Not available | No specific texture | None |
| G | Not available | No specific texture | None |

The example of Table I is simplified for ease of illustration. The general population may include a larger number of subjects, as do the experimental group, the control group and the target group. Moreover, although Table I shows a single secondary characteristic, more secondary characteristics may be used to train the AI system and/or to identify the subjects in the target group.

Table I illustrates a simple case in which there is a one-to-one correspondence between the specific criterion (amyloid positive or negative in the PET scan) and the secondary characteristic (specific texture indicative, or not, of amyloid being present in the brain). However, other examples may be contemplated. For a positive specific criterion related to another medical condition that is generally matched to positive values for secondary characteristics 'W', 'X', Y' and 'Z', this positive criterion may be matched, in a particular subject, to positive values for a subset of the secondary characteristics including 'W', 'X' and 'Y' and be matched, in another particular subject, to positive values for another subset of the secondary characteristics including 'W', 'Y' and 'Z'. The training of the AI system will improve as the number of test subjects who are made part of the experimental and control groups increases and as a number of secondary characteristics for the test subjects increases.

It is observed that a PET scan may also reveal the presence of tau protein in the brain of a subject. The detection of the tau protein in the brain of the subject may also indicate that the subject suffers from AD. Table I could be redrawn by replacing the term "amyloid" with "tau" or "amyloid and/or tau".

In an embodiment, instead of assigning (or not) the subjects of the general population to the target group when they are (or not) potentially affected by AD, the classifier may evaluate an amyloid status for one or more subjects or for all subjects of the general population. The evaluated amyloid status may be indicated as positive or negative in the global database 104, in the medical profiles of the subjects having had the evaluation. Providing a numerical value of the evaluated amyloid status for each subject of the general population, similar to the quantified value obtained from a PET scan, is also contemplated.

While AD and texture analysis of images of the retinas have been discussed in the above example, other examples presented hereinbelow will relate to other sources of ground truth information for defining positive and negative information for specific criterion for other medical conditions. Yet further examples will relate to other sources of information related to other secondary characteristics of the subjects in the general population.

Referring now to the drawings, FIG. 1 is a general architecture diagram of a network 100 adapted to acquire and process medical information according to an embodiment. The network 100 includes a patient management platform 102 that comprises a global database 104. The network 100 also includes an artificial system 106, a biomarker repository 108, and a plurality of medical modalities. The global database 104 contains medical profiles for a population of subjects known by the patient management platform 102. The AI system 106 may comprise a machine learning system or a deep learning system.

In an embodiment, the network 100 uses selectable and specific features present in multispectral retinal eye scans. To this end, one of the medical modalities includes a retinal eye scan system 110 located on premises, for example in an eye clinic. The retinal eye scan system 110 provides image features and anatomical features of the eyes of patients. The retinal eye scan system 110 is used by health care professionals assisted by eye technicians to obtain images of the retinas of patients. Other medical modalities include a pool of sources of adjunctive data of various types, for example a source 112 of Digital Medical Survey (DMS) results, a clinical study information repository 114, Electronic Medical Records (EMR) 116, and a portal 118 (for example an intelligent mobile terminal) transmitting signals, measurements and other information elements from sensors and other devices, including wearable devices. For example and without limitation, DMS results may include cognition test results, general health survey information, and the like. The clinical study information may include a list of specific medications prescribed to a patient, results of specific tests, and the like. EMR may include patient information such as gender, age, life style habits, drugs consumed by a patient, genetic information, and the like. Information obtained from wearable devices may include signals from cardiac monitors, sleep monitors, sensors installed in shoes to detect equilibrium problems for patients, and the like. Inclusion in the network 100 of additional adjunctive data sources is also contemplated.

The patient management platform 102 defines cohorts 120, 122 and 124 of subjects who have been subjected to tests that provide "ground truth" information in the form of positive or negative values for specific criteria for one or more specific medical conditions. All three cohorts 120, 122 and 124 are shown, the actual number of cohorts may be smaller or larger. In this context, a positive value may either be based on a binary detection for a specific criterion or based on a measured value exceeding a predetermined threshold for a specific criterion. When measured values are available for a specific criterion corresponding to a given medical condition, a gradation of the severity of that medical condition can be determined for the subjects of a cohort of subjects.

Information related to these cohorts is transmitted to the AI system 106. The AI system 106 is trained using this information and secondary characteristics of the subjects in the cohorts 120, 122 and 124 to learn to identify biomarkers that, when present in some subjects, reveal a potential that the subjects are affected by medical conditions related to those biomarkers. The AI system 106 stores information about the identified biomarkers in the biomarker repository 108.

The AI system 106 may extract secondary characteristics from related information, for example a multispectral medical image such as, for example, a retinal scan. In an embodiment, a deep learning system uses convolutional neural networks or an equivalent technique. The multispectral medical image has a high-dimensional structure that includes a combination of spatial and spectral information. The deep learning system is trained using a usually large number of multispectral medical images as training samples to construct the classifier. The AI system 106 first extracts key features from multispectral medical images. Key features that are significantly correlated with the specific condition are identified. When the classifier is constructed as a gradient boosted tree, multivariate modeling may then be undertaken.

The AI system 106 constructs a classifier 126 that can be applied to the global database 104 to identify, within the population of subjects and based on the presence of a given biomarker, particular subjects who may be impacted by a given medical condition. In a non-limiting embodiment, the AI system 106 uses the key features extracted from the multispectral medical images to construct the classifier 126, which can thus learn to detect the given biomarker. The classifier 126 may scale up as new features are extracted and provided of the AI system 106. As a result, medical reports 128 are issued by the AI system 106 for the particular subjects. The medical reports 128 may confirm the presence of the given biomarker in the particular subjects, who are then marked, in the global database 104 as members of a target group of subjects who are potentially affected by the given medical condition.

A non-limiting example of an application of the network 100 will now be presented. Some inputs of data to the patient management platform 102 may be related to subjects (patients) participating in clinical studies. Other inputs of data to the patient management platform 102 may be related to subjects of the general population who would benefit from advances in the detection of specific criteria for various medical conditions, for example the detection of various biomarkers.

The present example involves the transfer of retinal eye scans for a subject, from the retinal eye scan system 110 to the patient management platform 102. The patient management platform 102 handles the management of the identity of the subject. Data related to this subject and to other subjects having granted access to their data may be transferred to the patient management platform 102 from the source 112 of DMS results, from the clinical study information repository 114, from the EMR 116 and from the portal 118, for example with the help of intelligent mobile terminals.

Controlled cohorts 120, 122, 124 of subjects whose specific health conditions (e.g. subjects having various manifestations in their retinas) are known are provided to build and train the classifier 126 using an algorithm executed by the AI system 106. The AI system 106 may fetch information about specific subjects from the global database 104 through a query, allowing the AI system 106 to identify and segregate those subjects who share specific conditions to create ground truth information for constructing the classifier 126. Training of the AI system 106 may be an iterative process so that the performance of the classifier 126 improves as new and modified data for current and new subjects is added in the global data base 104.

Once the trained AI system 106 has constructed the classifier 126, retinal eye scans of new subjects may be acquired and processed by the classifier 126 to detect, in the retinas of these subjects, eventual signs of the presence of different biomarkers. Subjects whose information was not used to train the system 106 for a specific biomarker may benefit from the present technology to detect evidence of the presence of that specific biomarker. This present technology is scalable because, as the global database 104 grows, new biomarkers can be added to the biomarker repository 108 and become available to the general population of subjects. Presence or absence of specific biomarkers gives valuable information in the diagnostic of different eye diseases or systemic diseases that have manifestations in the eye, for example Alzheimer's disease, Parkinson's disease, multiple sclerosis, diabetes, vascular dementia, Lewis Body dementia, amyotrophic lateral sclerosis (ALS), and some specific cardiovascular diseases. Subjects who are identified as potentially affected by a given medical condition are identified as members of a target group for the given medical condition. Medical reports for these subjects may be sent for storage in the global database 104 of the patient management platform 102, the medical reports carrying information about the eventual presence of specific biomarkers. Health care professionals may get access to these medical reports through a login in the patient management platform 102.

The information contained in the network 100 is evolutionary in the sense that the amount and the precision of the information stored in the global database 104 will grow as new subjects are added in the population stored in the global database 104 and as new information is added for existing subjects of the population. In view of this growth, the classifier 126 may be updated and improved via re-training of the AI system 106 when the growth provides additional information of the type used to initially construct the classifier 126 and/or when the growth provides additional information related to the test subjects whose information has been used to construct the classifier 126. New specific criteria (for example previously undetected biomarkers) may be identified, and new cohorts may be defined for new medical conditions. The AI system 106 may be trained using this further information to construct new classifiers 130, 132 for the new medical conditions. As the new classifiers 130, 132 are constructed for the new medical conditions, they can be applied to the existing population of the global database 104 in view of identifying, among the population, new target groups of subjects who may be potentially impacted by the new medical condition. Although FIG. 1 shows three classifiers 126, 130 and 132, the actual number of classifiers may be smaller or larger.

Figure 2A:
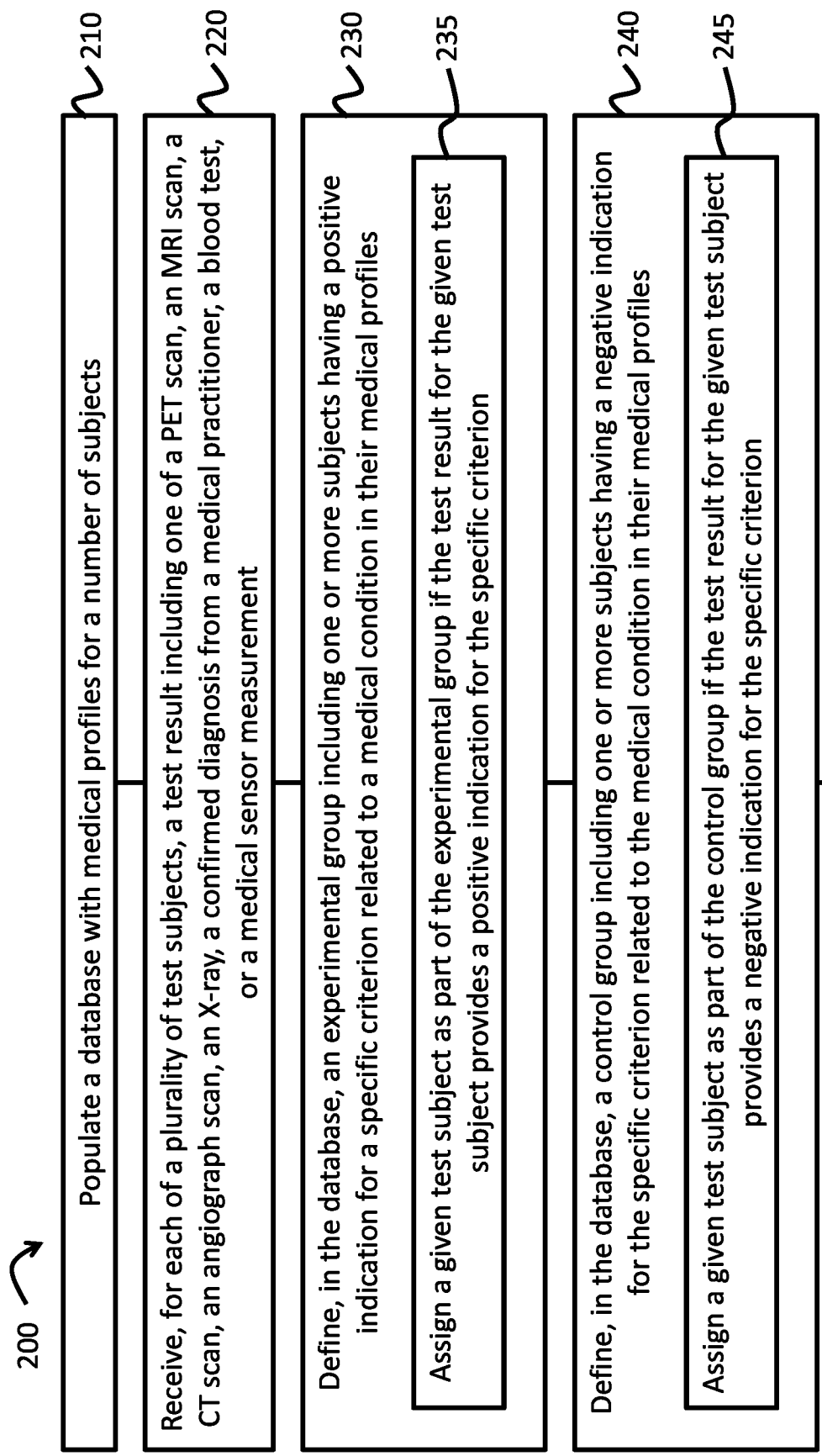
FIGS. 2a and 2b are a sequence diagram showing operations of a method for identifying subjects who are potentially impacted by a medical condition according to an embodiment.
Figure 2B:
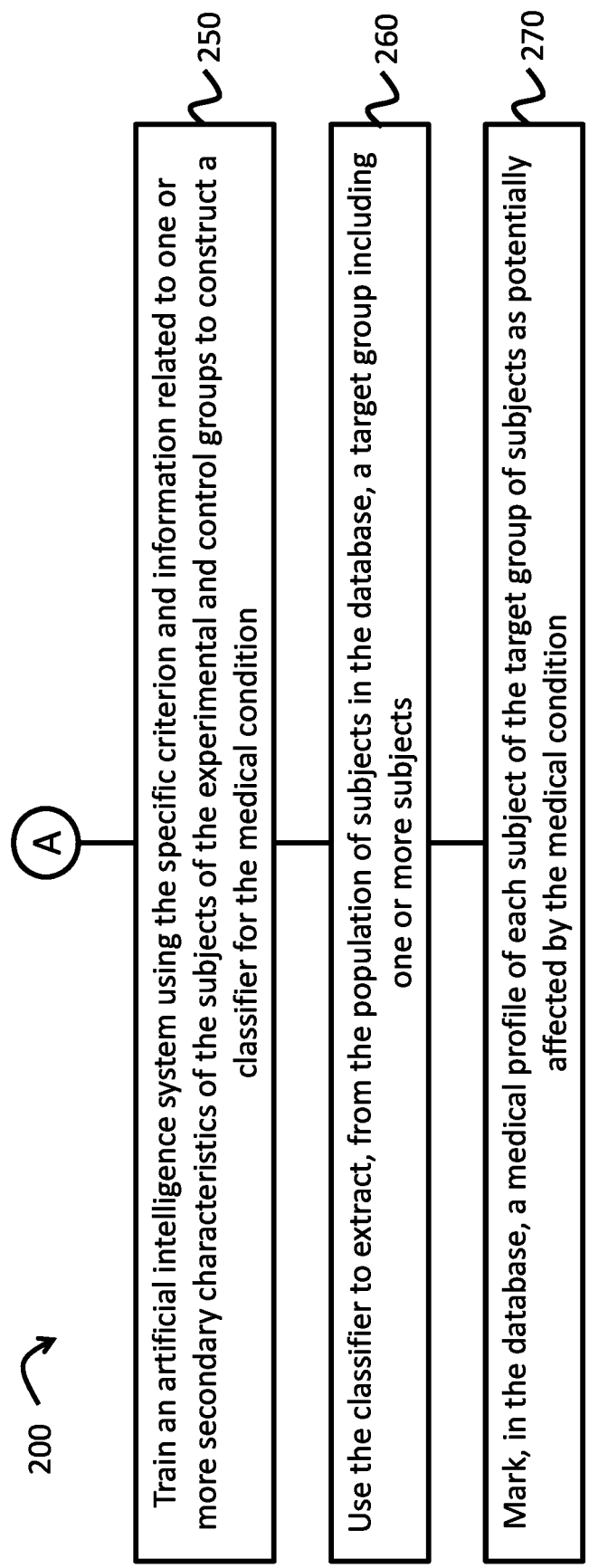

FIGS. 2*a* and 2*b* are a sequence diagram showing operations of a method for identifying subjects who are potentially impacted by a medical condition according to an embodiment. On FIGS. 2*a* and 2*b*, a sequence 200 comprises a plurality of operations, some of which may be executed in variable order, some of the operations possibly being executed concurrently, some of the operations being optional.

Starting on FIG. 2*a*, the global database 104 is populated with medical profiles for a number of subjects at operation 210. At operation 220, a test result is received at the patient management platform 102 for each of a plurality of test subjects forming a subset of the population of subjects. The test result is received from one of the medical modalities of the network 100. For example, the test results may be obtained via a PET scan, a magnetic resonance imaging (MRI) scan, a computerized tomography (CT) scan, an angiography scan, an X-ray, an ultrasonography test, a optical coherence tomography test, an endoscopy test, a confirmed clinical diagnosis from a medical practitioner, a blood test, a visual reading from a medical device, or a test providing an electric signal measurement from a medical sensor. An experimental group including one or more subjects having a positive indication for a specific criterion related to a medical condition in their medical profiles is defined in the global database 104 at operation 230. Operation 230 may comprise sub-operation 235 in which a given test subject is assigned as part of the experimental group if the test result for the given test subject provides a positive indication for the specific criterion. A control group including one or more subjects having a negative indication for the specific criterion related to the medical condition in their medical profiles is defined in the global database 104 at operation 240. Operation 240 may comprise sub-operation 245 in which a given test subject is assigned as part of the control group if the test result for the given test subject provides a negative indication for the specific criterion.

Continuing on FIG. 2b, the AI system 106 is trained at operation 250 using the specific criterion and one or more secondary characteristics of the subjects of the experimental and control groups to construct a classifier for the medical condition. Then at operation 260, the classifier is used to extract, from the population of subjects in the global database 104, a target group including one or more subjects. A medical profile of each subject of the target group of subjects is marked as potentially affected by the medical condition in the database 104 at operation 270.

In an embodiment, the target group may be made to exclude the subjects of the experimental group because the subjects of the experimental group are known to be affected by the medical condition. Likewise, the classifier is not expected to designate subjects of the control group as part of the target group because the subjects of the control group are known to be free from the medical condition. For members of the experimental group, a mark that these members are "potentially affected by the medical condition" may be construed as redundant and may be ignored. For members of the control group, such a mark may be incorrect and result from a corner case or from insufficient training of the AI system 106, in which case it may simply be ignored.

The sequence 200 may be executed a plurality of times in the network 100. In a non-limiting example, the medical condition mentioned in the above description of the sequence 200 may be AD, the specific criterion may relate to positive or negative detection of amyloid via a PET scan, and at least one secondary characteristic may relate to a texture analysis of the retina of various subjects. The same sequence 200 may be executed in view of identifying subjects who are potentially suffering from other medical conditions, for example Parkinson's disease, multiple sclerosis, diabetes, or specific cardiovascular diseases, all of which have manifestations that may be detected in the eye of a subject. Diabetes may be positively diagnosed through the evaluation of glucose levels in the blood in view of a predetermined criterion, for example a fasting plasma glucose level being greater than 7.0 mmol/liter. There is currently no known definite test for diagnosis of conditions such as Parkinson's disease, multiple sclerosis, Lewis Body dementia, vascular dementia and amyotrophic lateral sclerosis (ALS). A clinical diagnosis from a medical practitioner basing his/her findings on a number of clinical factors may be used as forming the positive or negative indication (ground truth) Parkinson's disease or for multiple sclerosis. The current state of research suggests that the detection of alpha-synuclein manifestations in the blood of a subject may eventually be used to positively identify Parkinson's disease and Lewis Body dementia. Diabetes, Parkinson's disease, multiple sclerosis, vascular dementia, Lewis Body dementia, and amyotrophic lateral sclerosis (ALS) are all known to cause artefacts that may be detected through the use of retina image analysis and provide information related to the secondary characteristics used to train the AI system 106.

Other sources of ground truth information for defining positive and negative information for specific criteria for other medical conditions may include, for example, results of blood tests, diagnosis from a medical practitioner (doctor), MRI scans, angiography scan, X-rays, an ultrasonography test, a optical coherence tomography test, an endoscopy test, a visual reading from a medical device, and electric signal measurements from medical sensors, for example wearable sensors. Depending on the particular medical condition, various medical modalities may provide positive and negative values for various types of specific criteria and/or provide various types of secondary characteristics. The sequence 200 may be executed at least once for each distinct specific criterion to cause the AI system 106 to construct a corresponding, distinct classifier and to identify distinct target groups for distinct medical conditions.

Figure 3:
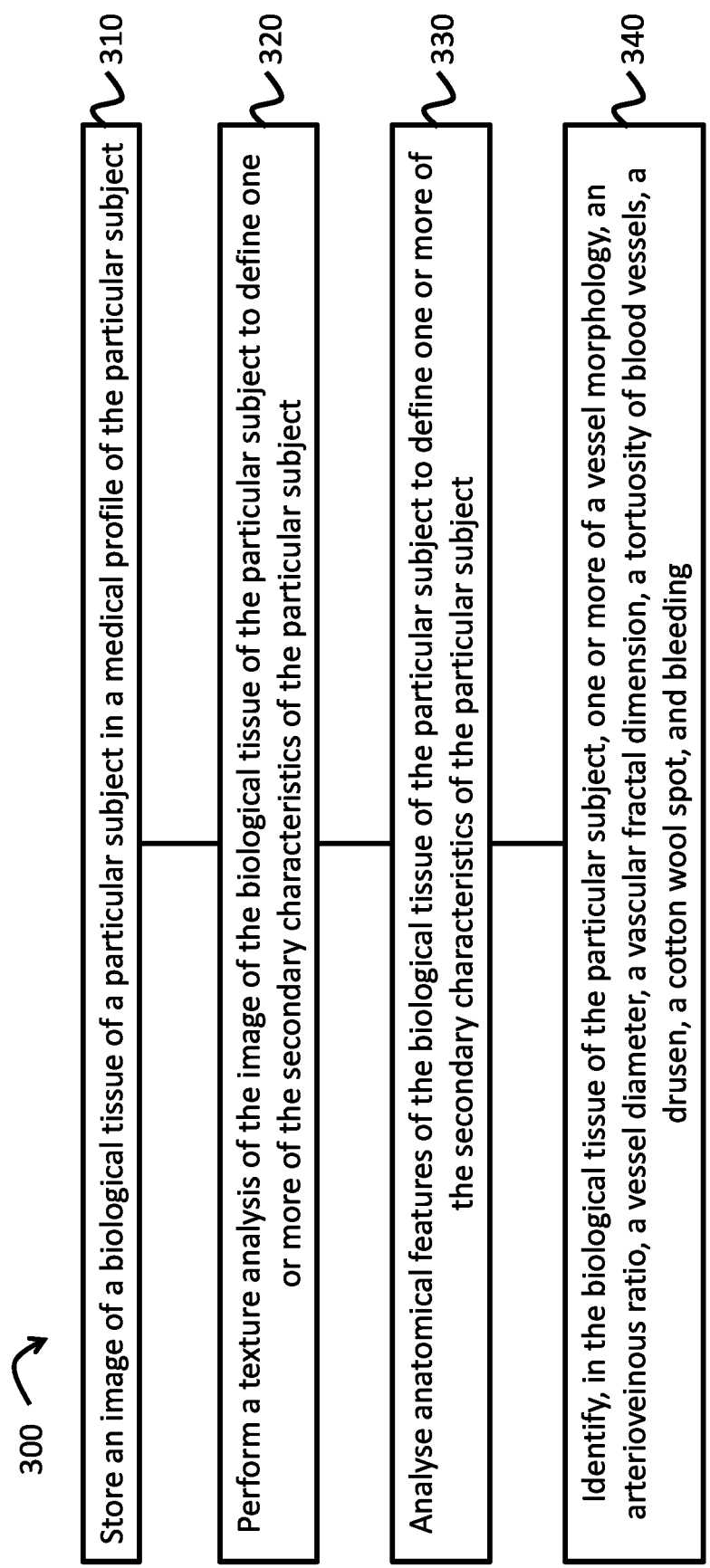
FIG. 3 is a sequence diagram showing operations of a method for treating an image of a biological tissue according to an embodiment.

As mentioned earlier, certain secondary characteristics may be identified via imaging of a biological tissue, for example a retina of a subject. FIG. 3 is a sequence diagram showing operations of a method for treating an image of a biological tissue according to an embodiment. On FIG. 3, a sequence 300 comprises a plurality of operations, some of which may be executed in variable order, some of the operations possibly being executed concurrently, some of the operations being optional. At operation 310, the patient management platform 102 receives an image of a biological tissue of a particular subject from one of the medical modalities of FIG. 1 and stores the image of the biological tissue of the particular subject in the medical profile of the particular subject, in the global database 104. In a non-limiting example, the biological tissue is a retina of the particular subject, the image being received at the patient management platform 102 from the retinal eye scan system 110.

A texture analysis of the image of the biological tissue of the particular subject may be performed at operation 320 to define one or more of the secondary characteristics of the particular subject at operation 340. Alternatively, or in addition to the texture analysis performed at operation 320, various anatomical features of the image of the biological tissue may be analyzed at operation 330 in view of defining one or more of the secondary characteristics of the particular subject at operation 340. Non-limiting examples of such anatomical features that may be identified at operation 340 include one or more of an optic nerve head morphology, a vessel morphology, an arterioveinous ratio, a vessel diameter, a vascular fractal dimension, a tortuosity of blood vessels, a druse, an exudate, a bifurcation coefficient, a bifurcation angle, a bifurcation asymmetry, arteriovenous nicking, a thickness of a retina structure, an area of a foveal avascular zone, a blood capillary density, a blood perfusion density, an optic nerve head disk diameter, an optic nerve head disk area, an optic nerve head cup diameter, an optic nerve head cup area, an eye movement, and an hemorrhage.

In an embodiment, one or more of the operations of the sequence 300 may be executed by a deep learning system comprised in the AI system 106.

Other secondary characteristics being part of the medical profiles of particular subjects may be provided to the patient management platform 102 and further to the AI system 106 by one of the medical modalities shown on FIG. 1. In non-limiting examples, such secondary characteristics for a particular subject may include one or more of an indication that a specific gene or group of genes is present or absent in a genotype of the particular subject, an age of the particular subject, a gender of the particular subject, a height of the particular subject, a weight of the particular subject, a list of medications prescribed to the particular subject, a blood pressure level of the particular subject, a cholesterol level of the particular subject, a blood glucose level of the particular subject, an image obtained by structural neuroimaging, a lifestyle factor, a body mass index, a set of administrative claims data, and an assessment obtained for the particular subject from a cognitive function evaluation, for example a cognitive test. It is contemplated that further types of medical information that may be expressed in logical form (being true or false, or being positive or negative) or that may be expressed in numerical form may also be used to define secondary characteristics for an subject in the population of the global database 104.

Figure 4:
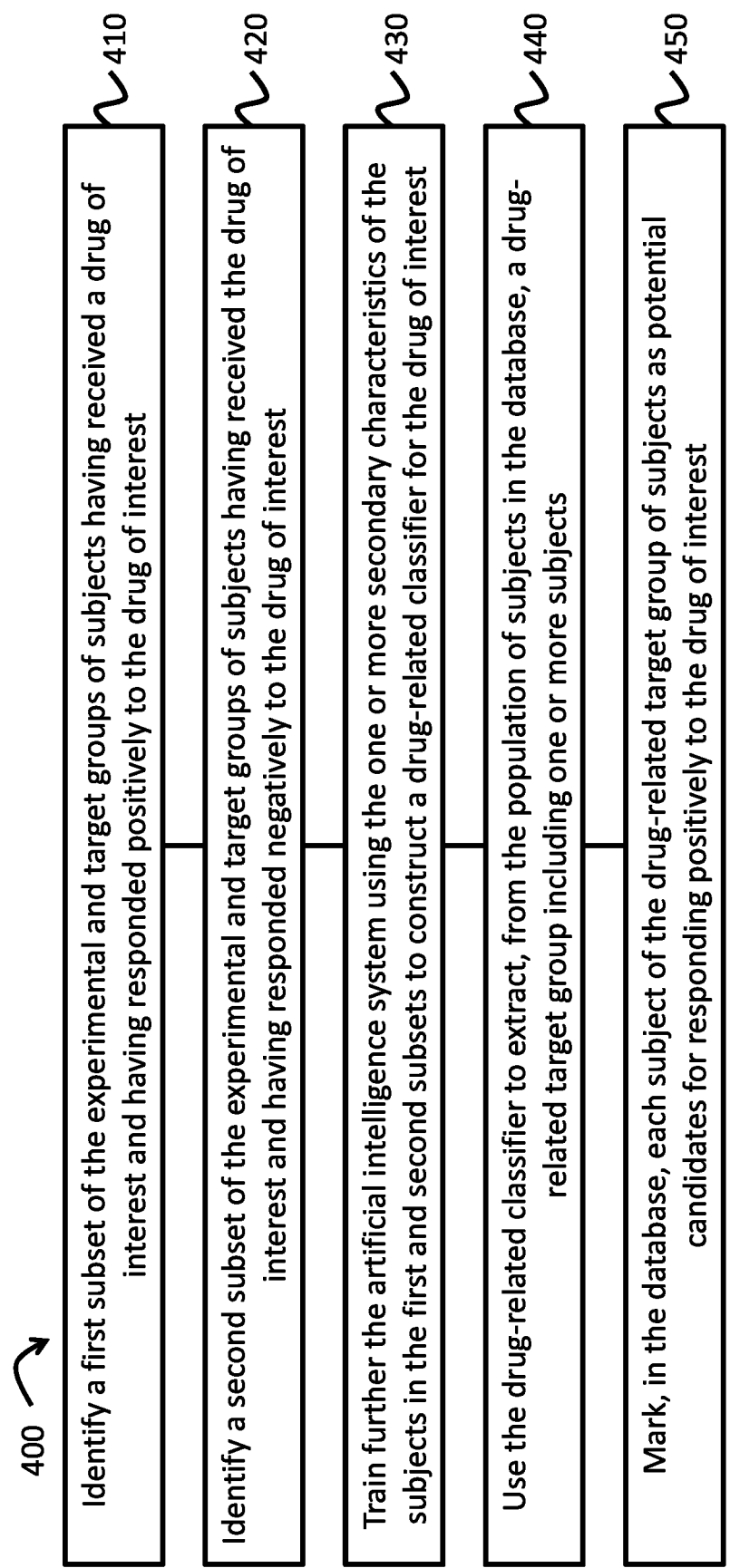
FIG. 4 is a sequence diagram showing operations of a method for identifying good responders to a drug of interest according to an embodiment.

As mentioned hereinabove, the AI system 106 may be trained with further information to construct additional classifiers 130, 132. For example, FIG. 4 is a sequence diagram showing operations of a method for identifying good responders to a drug of interest according to an embodiment. On FIG. 4, a sequence 400 comprises a plurality of operations, some of which may be executed in variable order, some of the operations possibly being executed concurrently, some of the operations being optional. The sequence 400 may involve members of the experimental group who are defined at operation 230 (FIG. 2*a*) based on their positive indication for a specific criterion for a medical condition, and members of the target group who are identified at operation 260 (FIG. 2*b*) and marked at operation 270 (FIG. 2*b*) as potentially affected by the medical condition. In a non-limiting example, the subjects of the experimental group are affected by AD, their diagnosis being obtained via PET scans having revealed the presence of amyloid in their brains, and textures indicative of the present of amyloid in their brains have been detected in the retinas of the subjects of the target group. Some of these subjects have been prescribed a drug of interest, having led to improvements in the condition of some subjects and not in other subjects.

A first subset of the experimental and target groups of subjects having received the drug of interest and having responded positively to the drug of interest is identified at operation 410. Conversely, a second subset of the experimental and target groups of subjects having received the drug of interest and having responded negatively to the drug of interest is identified at operation 420. The AI system 106 is trained further at operation 430, using the one or more secondary characteristics of the subjects in the first and second subsets, to construct a drug-related classifier for the drug of interest. The drug-related classifier is not the classifier 126 constructed at operation 250 (FIG. 2*b*), but may be one of the classifiers 130 or 132. At operation 440, the drug-related classifier is used to extract, among the population of subjects in the global database 104, a drug-related target group including one or more subjects, the drug-related target group optionally excluding the subjects of the first and second subsets. Alternatively at operation 440, the drug-related classifier may be applied to the subjects of the experimental and target groups only because the subjects in these groups are more likely to benefit from receiving the drug of interest for treatment of the medical condition applicable to the sequence 200 (FIGS. 2*a* and 2*b*). Then at operation 260, each subject of the drug-related target group of subjects is marked, in the global database 104, as potential candidates for responding positively to the drug of interest.

Figure 5:
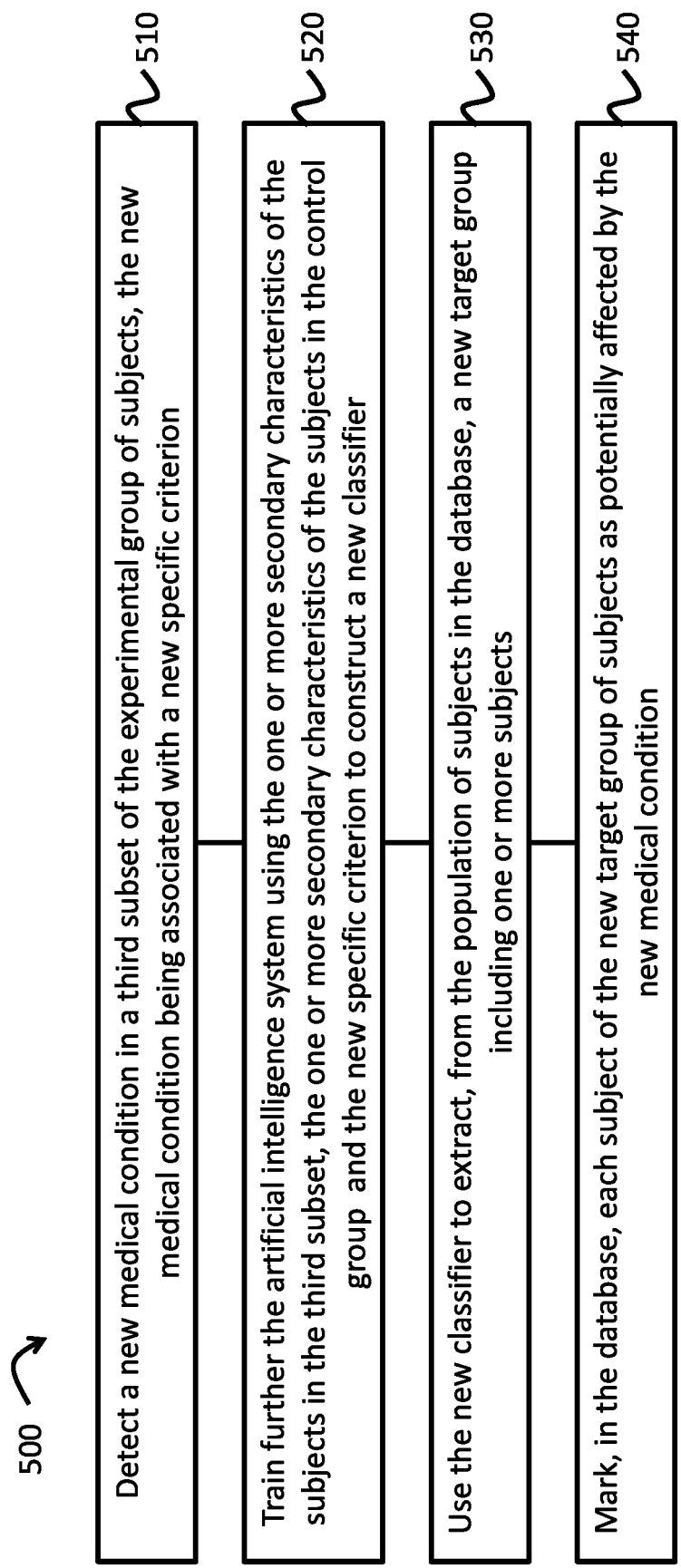
FIG. 5 is a sequence diagram showing operations of a method for identifying a group of subject potentially affected by a new medical condition according to an embodiment.

It has been observed that persons affected by a given medical condition are frequently affected by another medical condition. The relationship between medical conditions may be observed empirically by physicians, but may nevertheless be difficult to predict. Another example of further information that may be used to train the AI system 106 is shown on FIG. 5, which is a sequence diagram showing operations of a method for identifying a group of subject potentially affected by a new medical condition according to an embodiment. On FIG. 5, a sequence 500 comprises a plurality of operations, some of which may be executed in variable order, some of the operations possibly being executed concurrently, some of the operations being optional. As in the case of FIG. 4, the sequence 500 may involve members of the experimental group who are defined at operation 230 (FIG. 2*a*) based on their positive indication for a specific criterion for a medical condition, and members of the target group who are identified at operation 260 (FIG. 2*b*) and marked at operation 270 (FIG. 2*b*) as potentially affected by the medical condition.

At operation 510, a new medical condition is detected in a third subset of the experimental group of subjects. This new medical condition is associated with a new specific criterion. As a non-limiting example, the new medical condition may be a cardiovascular disease, the given subject having suffered from a heart attack, and the new specific criterion may be related to arteriosclerosis. The AI system 106 is trained further at operation 520 using the one or more secondary characteristics of the subjects in the third subset, the one or more secondary characteristics of the subjects in the control group and the new specific criterion to construct a new classifier. In an embodiment, the new classifier may be constructed when a number of subjects in the third subset of the experimental group of subjects having the new medical condition is deemed sufficient to further train the AI system 106.

The new classifier constructed at operation 520 is distinct from the classifier 126 (FIG. 1) constructed at operation 250 (FIG. 2*b*). In the arteriosclerosis example, the new classifier is constructed to identify the subjects of the experimental group who are at risk of cardiovascular disease. The new classifier is used at operation 530 to extract, among the population of subjects in the global database 104, a new target group including one or more subjects. Alternatively at operation 530, the new classifier may be applied to the subjects of the experimental group only because the new classifier can identify subjects in this group that are likely to be affected by both the medical condition applicable to the sequence 200 (FIGS. 2*a* and 2*b*) and the new medical condition. At operation 540, each subject of the new target group of subjects is marked in the global database 104 as potentially affected by the new medical condition.

Returning to FIGS. 2*a* and 2*b*, once the sequence 200 has been executed for a given medical condition and the medical profile of each subject to the target group of subjects has been marked as potentially affected by the given medical condition, other events may lead to re-training the AI system 106 and to updating the classier for the given medical condition. As will be described below in relation to FIGS. 6 and 7, the AI system 106 may be re-trained as new information is received at the patient management platform 102 and at the AI system 106. In an embodiment, the operations described in relation to FIGS. 6 and/or 7 may be executed each time new information is received. In another embodiment, these operations may be executed at regular interval or based on an external trigger.

Figure 6:
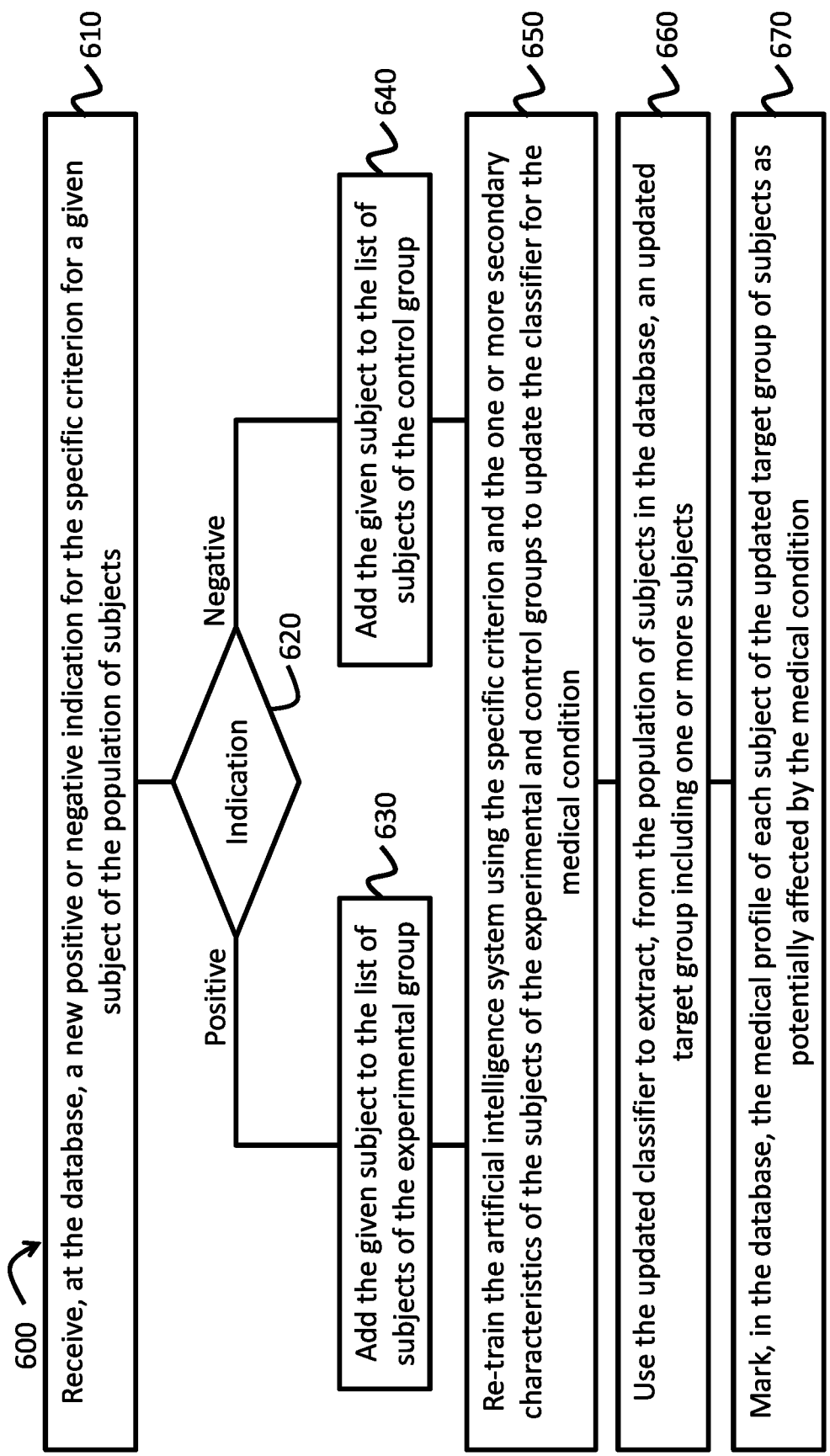
FIG. 6 is a sequence diagram showing operations of a first method for re-training an artificial intelligence system according to an embodiment.

FIG. 6 is a sequence diagram showing operations of a first method for re-training an artificial intelligence system according to an embodiment. On FIG. 6, a sequence 600 comprises a plurality of operations, some of which may be executed in variable order, some of the operations possibly being executed concurrently, some of the operations being optional. The sequence 600 is concerned with the addition of a given subject in one of the experimental group and the control group for the given medical condition addressed in the sequence 200 (FIGS. 2*a* and 2*b*).

At operation 610, the patient management platform 102 and, more particularly, the global database 104, receive a new positive or negative indication for the specific criterion for a given subject of the population of subjects. The value of the indication is verified at operation 620. If the indication is positive, the given subject is added to the list of subjects of the experimental group at operation 630. If the indication is negative, the given subject is added to the list of subjects of the control group at operation 640. In either case, the artificial intelligence system is retrained at operation 650 using the specific criterion and the one or more secondary characteristics of the subjects of the experimental and control groups to update the classifier 126 for the medical condition. At this point, it may be noted that either the experimental or control group has been modified by operations 610 to 640. There should therefore be at least some new or modified information that may impact the re-training of the AI system 106.

At operation 660, the updated classifier is used to extract, from the population of subjects in the global database 104, an updated target group including one or more subjects, the updated target group optionally excluding the subjects of the experimental and control groups. The medical profile of each subject of the updated target group of subjects is marked, in the global database 104, as potentially affected by the medical condition at operation 670.

In an embodiment, the sequence 600 may be executed at once from operation 610 to operation 670. In another embodiment, the sequence 600 may be paused temporarily after operations 630 or 640 so that the AI system 106 is re-trained, at operation 650, on a regular basis or when a sufficient number of subjects has been added in one of the experimental or control group by repeating operations 610 to 640. Other modifications of the sequence 600 leading to the re-training of the AI system 106 are also contemplated. For example, the sequence 600 may be adjusted so that the AI system 106 is re-trained more frequently when the number of subjects in the experimental group and/or in the control group is less than a predetermined number of subjects.

Figure 7:
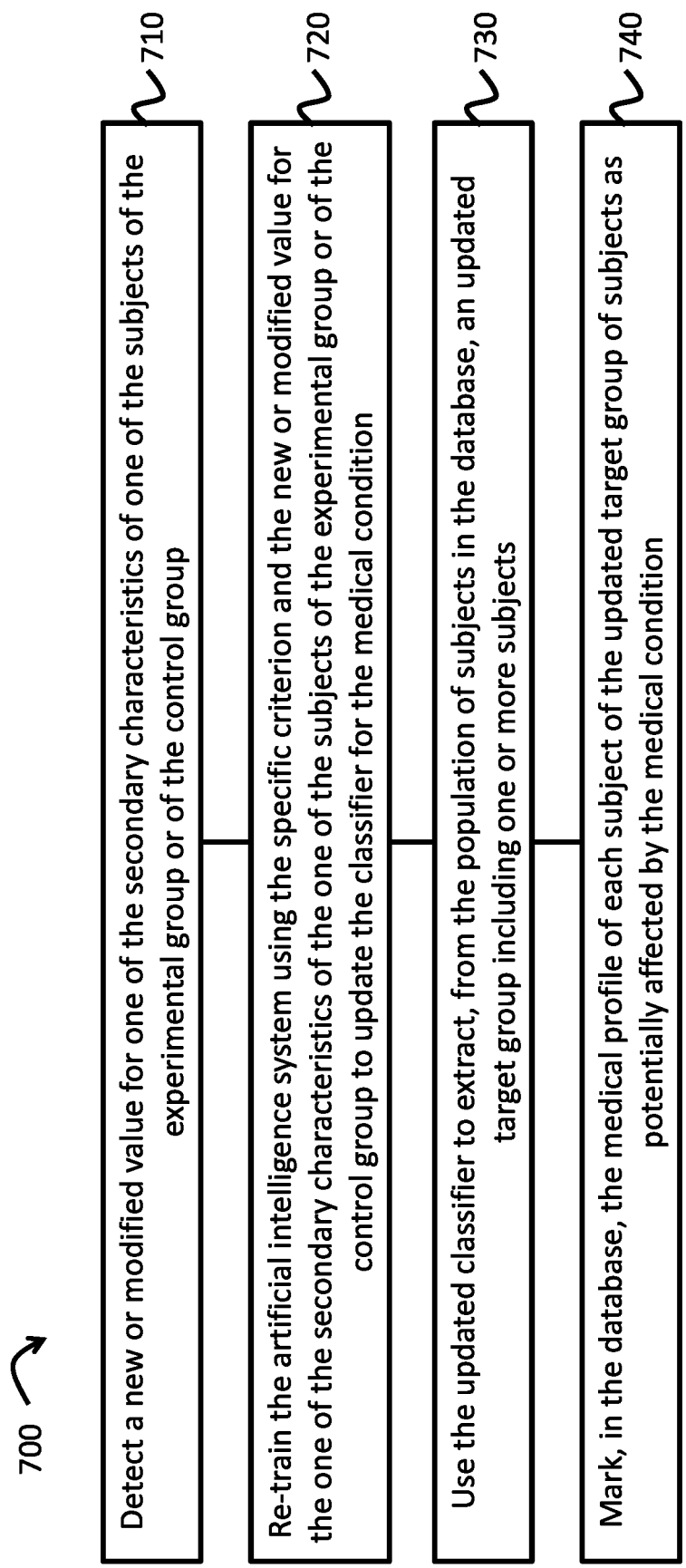
FIG. 7 is a sequence diagram showing operations of a second method for re-training an artificial intelligence system according to an embodiment.

FIG. 7 is a sequence diagram showing operations of a second method for re-training an artificial intelligence system according to an embodiment. On FIG. 7, a sequence 700 comprises a plurality of operations, some of which may be executed in variable order, some of the operations possibly being executed concurrently, some of the operations being optional. As in the case of the sequence 600 (FIG. 6), the sequence 700 follows the execution of the sequence 200 (FIGS. 2a and 2b). The sequence 700 is concerned with changes of secondary characteristics for subjects in the experimental group and in the control group for any given medical condition addressed in the sequence 200 (FIGS. 2a and 2b).

At operation 610, the patient management platform 102 and, more particularly, the global database 104, are informed of a detected new or modified value for one of the secondary characteristics of one of the subjects of the experimental group or of the control group. The AI system 106 is retrained at operation 720 using the specific criterion and the new or modified value for the one of the secondary characteristics of the one of the subjects of the experimental group or of the control group to update the classifier 126 for the medical condition. The updated classifier is used at operation 730 to extract, from the population of subjects in the global database 104, an updated target group including one or more subjects. The medical profile of each subject of the updated target group of subjects is marked, in the global database 104, as potentially affected by the medical condition at operation 740.

As in the case of the FIG. 6, the sequence 700 is not necessarily executed at once following operation 710. The AI system 106 may be re-trained at operation 720 are various intervals or based on various conditions.

Figure 8:
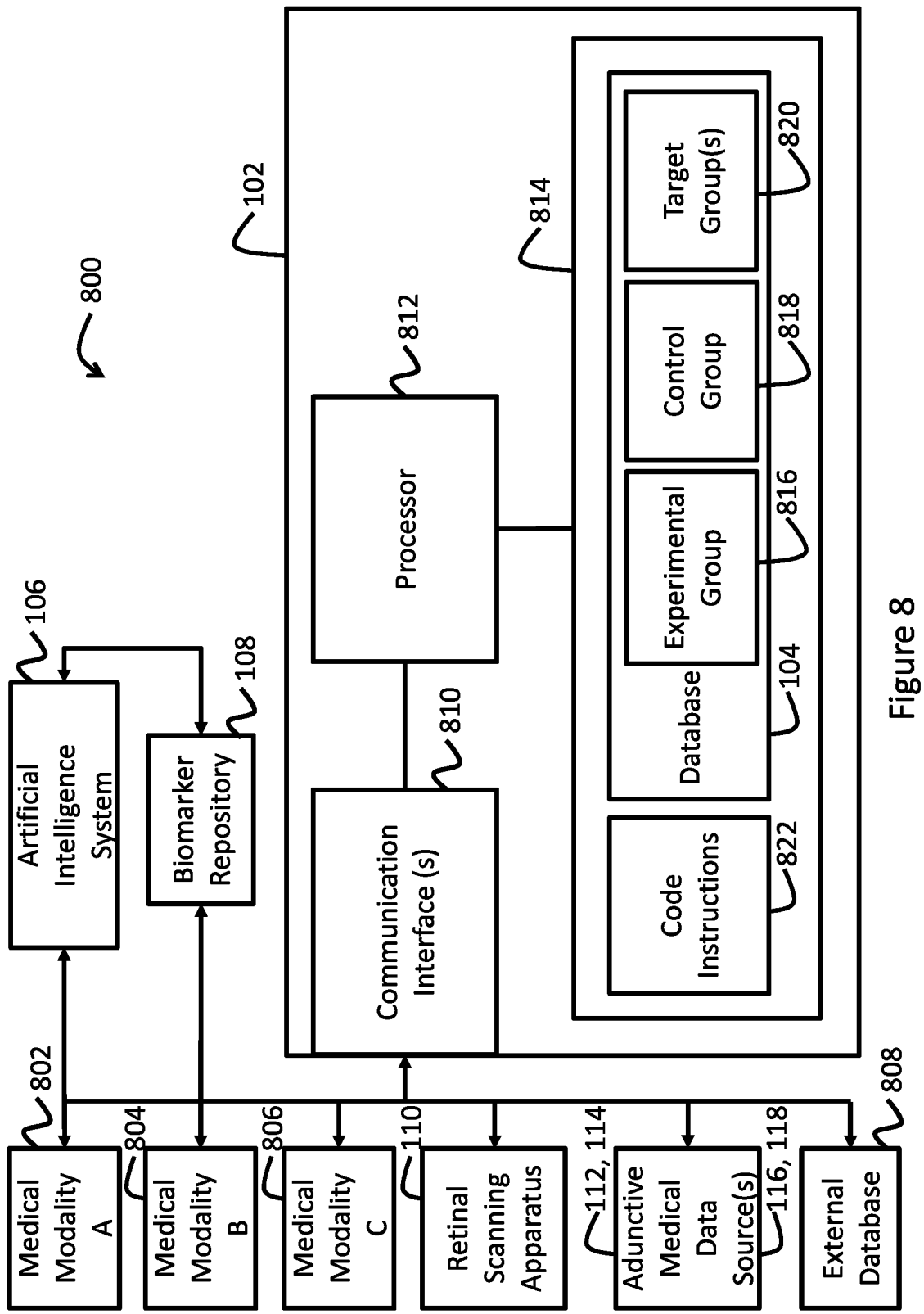
FIG. 8 is a simplified block diagram of a system for identifying subjects who are potentially impacted by a medical condition according to an embodiment.

Each of the operations of the sequences 200, 300, 400, 500, 600 and 700 may be configured to be processed by one or more processors, the one or more processors being coupled to a memory device. For example, FIG. 8 is a simplified block diagram of a system 800 for identifying subjects who are potentially impacted by a medical condition according to an embodiment. The system 800 includes the patient management platform 102 and its global database 104, the AI system 106, the biomarker repository 108, the retinal eye scan system 110, the source 112 of DMS results, the clinical study information repository 114, the EMR 116 and the portal 118. The system may also comprise additional medical modalities 802, 804 and 806, and an external database 808. The medical modalities 802, 804 and 806 may provide various types of medical information such, for example, PET scans, blood test results, electric signal measurements from medical sensors, and the like. The patient management platform 102 communicates with the AI system 106, the biomarker repository 108, the retinal eye scan system 110, the source 112 of DMS results, the clinical study information repository 114, the EMR 116, the portal 118, the additional medical modalities 802, 804 and 806, and the external database 808 via a communication interface 810.

In addition to the communication interface 810, the patient management platform 102 includes a processor 812 and a memory device 814. The processor 812 is a controller for the patient management platform 102 and for the system 800 as a whole. The processor 812 is operatively connected to the memory device 814, to the communication interface 810 and, through the communication interface 810, to other components of the system 800. It is contemplated that the memory device 814 could be split into multiple memory devices and/or storage units. Similarly it is contemplated that the processor 812 could include a plurality of cooperating processors. The communication interface 810 may include a plurality of communication devices adapted for communicating with components of the system 800 outside of the patient management platform 102, distinct communication devices using distinct network interface technologies and distinct communication protocols, as required for compatibility with these components of the system 800.

In the illustrated, non-limiting embodiment of FIG. 8, the global database 104 is integrated in the memory device 814. The global database 104 includes partitions 816, 818 and 820 for respectively storing lists of subjects of the experimental, control and target groups along with their medical information. The memory 814 also includes a non-transitory computer-readable medium 822 having stored thereon machine executable instructions for performing, when executed by the processor 812, at least some of the operations of the sequences 200, 300, 400, 500, 600 and 700. Some or all of these operations may be performed by the processor 812. Alternatively, some of these operations may be performed by other components of the system 800, including without limitation by the AI system 106.

In operation, the system 800 for identifying subjects who are potentially impacted by a medical condition may perform as follows. The global database 104 stores medical profiles for a population of subjects. The communication interface 810 receives positive and negative indications for a specific criterion related to the medical condition, for a subset of the population of subjects, from one or more of the medical modalities 802, 804 or 806. The communication interface 810 receives one or more secondary characteristics for the population of subjects from the retinal eye scan system 110, from one or more of the medical modalities 802, 804 or 806, and/or from one or more of the source 112 of DMS results, the clinical study information repository 114, the EMR 116 and the portal 118.

Non-limiting examples of the one or more secondary characteristics provided by the one or more second medical modalities include, for a particular subject, a result of a texture analysis of an image of a biological tissue of the particular subject, a result of a vessel morphology analysis of the image of the biological tissue of the particular subject, an indication that a specific gene or group of genes is present or absent in a genotype of the particular subject, an age of the particular subject, a gender of the particular subject, a height of the particular subject, a weight of the particular subject, a list of medications prescribed to the particular subject, a blood pressure level of the particular subject, a cholesterol level of the particular subject, an image obtained by structural neuroimaging, a lifestyle factor, a body mass index, a set of administrative claims data, a blood glucose level of the particular subject, and an assessment obtained for the particular subject from a cognitive function evaluation, for example a cognitive test.

The processor 812 defines, in the global database 104, the experimental group 816 including one or more subjects having the positive indication for the specific criterion in their medical profiles. The processor 812 also defines, in the global database 104, the control group 104 including one or more subjects having the negative indication for the specific criterion in their medical profiles. The processor 812 provides, via the communication interface 810, the specific criterion and one or more secondary characteristics of the subjects of the experimental and control groups to the AI system 106.

The AI system 106 constructs the classifier 126 (FIG. 1) for the medical condition based on a provided criterion and on the provided list of characteristics. The AI system 106 may store information about the provided criterion, which generally identifies a biomarker, in the biomarker repository 108. The AI system 106 uses the classifier to extract, from the population of subjects in the global database 104, a target group including one or more subjects. For this, the AI system 106 may fetch information about the subjects in the global database 104 via the communication interface 810 and the processor 812. The processor 812 receives, via the communication interface 810, identifications of the subjects of the target group from the AI system 106. The processor 812 may remove any subjects of the experimental and control groups 816, 818 from the target group before storing remaining contents as the target group 820 in the global database 104. The processor 812 also marks, in the global database 104, the medical profile of each subject of the target group 820 of subjects as potentially affected by the medical condition.

Those of ordinary skill in the art will realize that the description of the method and system for identifying subjects who are potentially impacted by a medical condition are illustrative only and are not intended to be in any way limiting. Other embodiments will readily suggest themselves to such persons with ordinary skill in the art having the benefit of the present disclosure. Furthermore, the disclosed method and system may be customized to offer valuable solutions to existing needs and problems related to the underutilization of medical information related to subjects in the general population. In the interest of clarity, not all of the routine features of the implementations of the method and system are shown and described. In particular, combinations of features are not limited to those presented in the foregoing description as combinations of elements listed in the appended claims form an integral part of the present disclosure. It will, of course, be appreciated that in the development of any such actual implementation of the method and system, numerous implementation-specific decisions may need to be made in order to achieve the developer's specific goals, such as compliance with application-, system-, network-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of medical information having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer, a processor operatively connected to a memory device, or a machine, those operations may be stored as a series of instructions readable by the machine, processor or computer, and may be stored on a non-transitory, tangible medium.

Systems and modules described herein may comprise software, firmware, hardware, or any combination(s) of software, firmware, or hardware suitable for the purposes described herein. Software and other modules may be executed by a processor and reside on a memory device of servers, workstations, personal computers, computerized tablets, personal digital assistants (PDA), and other devices suitable for the purposes described herein. Software and other modules may be accessible via local memory device, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A method for identifying subjects who are potentially impacted by a medical condition, comprising:
defining, in a database containing medical profiles for a population of subjects, an experimental group including one or more first subjects having a positive indication for a specific criterion related to the medical condition in their medical profiles, the positive indication indicating that each of the one or more first subjects has been diagnosed as being affected by the medical condition via direct observation of the specific criterion, the medical condition being one of an eye disease and a systemic disease having manifestations in an eye of a subject;

defining, in the database, a control group including one or more second subjects having a negative indication for the specific criterion related to the medical condition in their medical profiles, the negative indication indicating that each of the one or more second subjects has been diagnosed as being unaffected by the medical condition via direct observation of the specific criterion;

using an eye scan system to acquire, for each first and second subject of the population of subjects, a multispectral image of a retina of the subject;

training an artificial intelligence system using the positive and negative indications for the specific criterion and information related to one or more secondary characteristics of the first subjects of the experimental group and of the second subjects of the control group to construct a classifier for the medical condition, the information related to the one or more secondary characteristics for a particular subject among the first and second subjects being obtained at least in part by analysis of the multispectral image of the retina of the particular subject;

using the classifier to extract, from the population of subjects in the database, a target group including one or more subjects; and marking, in the database, a medical profile of each subject of the target group of subjects as potentially affected by the medical condition.

2. The method of claim 1, wherein:
the positive indication for the specific criterion in a particular subject of the experimental group is related to the presence of a specific biomarker in the particular subject; and
the classifier is constructed to identify the subjects of the target group based on a likelihood of the presence of the specific biomarker in the subjects of the target group.

3. The method of claim 1, further comprising:
identifying a first subset of the experimental and target groups of subjects having received a drug of interest and having responded positively to the drug of interest;
identifying a second subset of the experimental and target groups of subjects having received the drug of interest and having responded negatively to the drug of interest;
training further the artificial intelligence system using the one or more secondary characteristics of the subjects in the first and second subsets to construct a drug-related classifier for the drug of interest;
using the drug-related classifier to extract, from the population of subjects in the database, a drug-related target group including one or more subjects; and
marking, in the database, each subject of the drug-related target group of subjects as potential candidates for responding positively to the drug of interest.

4. The method of claim 1, further comprising:
detecting a new medical condition in a third subset of the experimental group of subjects, the new medical condition being associated with a new specific criterion;
training further the artificial intelligence system using the one or more secondary characteristics of the subjects in the third subset, the one or more secondary characteristics of the subjects in the control group and the new specific criterion to construct a new classifier;

using the new classifier to extract, from the population of subjects in the database, a new target group including one or more subjects; and
marking, in the database, each subject of the new target group of subjects as potentially affected by the new medical condition.

5. The method of claim 1, further comprising:
following marking, in the database, the medical profile of each subject of the target group of subjects as potentially affected by the medical condition, receiving, at the database, a new positive or negative indication for the specific criterion for a given subject of the population of subjects; and
in response to receiving the new indication:
adding the given subject to the list of subjects of the experimental group if the new indication is a positive indication,
adding the given subject to the list of subjects of the control group if the new indication is a negative indication,
re-training the artificial intelligence system using the specific criterion and the one or more secondary characteristics of the subjects of the experimental and control groups to update the classifier for the medical condition,
using the updated classifier to extract, from the population of subjects in the database, an updated target group including one or more subjects, and
marking, in the database, the medical profile of each subject of the updated target group of subjects as potentially affected by the medical condition.

6. The method of claim 1, further comprising:
following marking, in the database, the medical profile of each subject of the target group of subjects as potentially affected by the medical condition, detecting a new or modified value for one of the secondary characteristics of one of the subjects of the experimental group or of the control group;
in response to receiving the new or modified value for the one of the secondary characteristics:
re-training the artificial intelligence system using the specific criterion and the new or modified value for the one of the secondary characteristics of the one of the subjects of the experimental group or of the control group to update the classifier for the medical condition;
using the updated classifier to extract, from the population of subjects in the database, an updated target group including one or more subjects; and
marking, in the database, the medical profile of each subject of the updated target group of subjects as potentially affected by the medical condition.

7. The method of claim 1, wherein the systemic disease having manifestations in the eyes of a subject is one of Alzheimer's disease, Parkinson's disease, multiple sclerosis, diabetes, vascular dementia, Lewis Body dementia, amyotrophic lateral sclerosis (ALS), and a cardiovascular disease.

8. A method for evaluating a potentiality of subjects for being affected by a medical condition, comprising:
defining, in a database containing medical profiles for a population of subjects, an experimental group including one or more first subjects having a positive indication for a specific criterion related to the medical condition in their medical profiles, the positive indication indicating that each of the one or more first subjects has been diagnosed as being affected by the medical condition via direct observation of the specific criterion, the positive indication for the specific criterion in each first subject of the experimental group being related to a confirmed presence of a specific biomarker in the first subject, the medical condition being one of an eye disease and a systemic disease having manifestations in an eye of a subject;

defining, in the database, a control group including one or more second subjects having a negative indication for the specific criterion related to the medical condition in their medical profiles, the negative indication indicating that each of the one or more second subjects has been diagnosed as being unaffected by the medical condition via direct observation of the specific criterion;

using an eye scan system to acquire, for each first and second subject of the population of subjects, a multispectral image of a retina of the subject:

training an artificial intelligence system using the positive and negative indications for the specific criterion and information related to one or more secondary characteristics of the first subjects of the experimental group and of the second subjects of the control group to construct a classifier for the medical condition, the information related to the one or more secondary characteristics for a particular subject among the first and second subjects being obtained at least in part by analysis of the multispectral image of the retina of the particular subject;

using the classifier to evaluate a potential of being affected by the medical condition for a given subject in the population of subjects, the classifier evaluating the potential for the given subject based on a likelihood of a presence of the specific biomarker in the given subject; and storing, in the database, the evaluated potential of being affected by the medical condition in a medical profile of the given subject.

9. The method of claim 8, further comprising:

receiving a test result for each of a plurality of test subjects forming a subset of the population of subjects, each test result being obtained using a test selected from a positron emission tomography scan, a magnetic resonance imaging scan, a computerized tomography scan, an angiography scan, an X-ray, an ultrasonography test, an optical coherence tomography test, an endoscopy test, a confirmed diagnosis from a medical practitioner, a blood test, a visual reading from a medical device, and a test providing an electric signal measurement from a medical sensor; and storing the test result for each test subject in a corresponding medical profile;

wherein a given test subject is part of the experimental group if the test result for the given test subject provides a positive indication for the specific criterion; and wherein the given test subject is part of the control group if the test result for the given test subject provides a negative indication for the specific criterion.

10. The method of claim 8, further comprising extracting a key feature from the multispectral image of a retina of a particular subject to define one of the one or more secondary characteristics of the particular subject.

11. The method of claim 8, further comprising analyzing anatomical features of the multispectral image of a retina of a particular subject to define one of the one or more secondary characteristics of the particular subject.

12. The method of claim 8, wherein at least one additional secondary characteristic in the medical profile of a particular subject comprises an indication that a specific gene or group of genes is present or absent in a genotype of the particular subject.

13. The method of claim 8, wherein at least one additional secondary characteristic in the medical profile of a particular subject comprises an element selected from an age of the particular subject, a gender of the particular subject, a height of the particular subject, a weight of the particular subject, a list of medications prescribed to the particular subject, a blood pressure level of the particular subject, a cholesterol level of the particular subject, a result of a blood test of the particular subject, a blood glucose level of the particular subject, an image obtained by structural neuroimaging, a lifestyle factor, a body mass index, a set of administrative claims data, an assessment obtained for the particular subject from a cognitive test, and a combination thereof.

14. The method of claim 8, wherein the evaluated potential comprises a positive or a negative indication of the given subject being potentially affected by the medical condition.

15. The method of claim 8, wherein the evaluated potential comprises a quantification of the potential for the given subject for being affected by the medical condition.

16. The method of claim 8, wherein the systemic disease having manifestations in the eyes of a subject is one of Alzheimer's disease, Parkinson's disease, multiple sclerosis, diabetes, vascular dementia, Lewis Body dementia, amyotrophic lateral sclerosis (ALS), and a cardiovascular disease.

17. A system for identifying subjects who are potentially impacted by a medical condition, comprising:

a database configured for storing medical profiles for a population of subjects;

an eye scan system configured to acquire, for each subject of the population of subjects, a multispectral image of a retina of the subject;

a communication interface configured for:

receiving, from a first medical modality, positive and negative indications for a specific criterion related to the medical condition for a subset of the population of subjects, the positive indication for a first particular subject indicating that the first particular subject has been diagnosed as being affected by the medical condition via direct observation of the specific criterion, the negative indication for a second particular subject indicating that the second particular subject has been diagnosed as being unaffected by the medical condition via direct observation of the specific criterion, the medical condition being one of an eye disease and a systemic disease having manifestations in an eye of a subject, and receiving, from the eye scan system, the multispectral image of the retina of each subject of the population of subjects;

an artificial intelligence system configured to:

extract information related to one or more secondary characteristics of each subject of the population of subjects by analysis of the multispectral image of the retina of the particular subject, be trained to construct a classifier for the medical condition by using (i) the positive and negative indications for the specific criterion, (ii) the information related to the one or more secondary characteristics of the subjects of an experimental group, the experimental group including one or more subjects having the positive indication for the specific criterion in their medical profiles, and (iii) the information related to the one or more secondary characteristics of the subjects of a control group, the control group including one or more subjects having the negative indication for the specific criterion in their medical profiles, and use the classifier to evaluate, for a given subject, a potential of being affected by the medical condition; and a controller operatively connected to the database, to the communication interface and to the artificial intelligence system, the controller being configured to:

define, in the database, the experimental group, define, in the database, the control group, provide the specific criterion to the artificial intelligence system, and store, in the database, the evaluated potential of being affected by the medical condition in a medical profile of the given subject.

18. The system of claim 17, wherein:

the first medical modality provides a test result for each of a plurality of test subjects forming the subset of the population of subjects, each test result being obtained using a test selected from a positron emission tomography scan, a magnetic resonance imaging scan, a computerized tomography scan, an angiography scan, an X-ray, an ultrasonography test, an optical coherence tomography test, an endoscopy test, a confirmed diagnosis from a medical practitioner, a blood test, a visual reading from a medical device, and a test providing an electric signal measurement from a medical sensor; and the one or more secondary characteristics include, for a particular subject, an element selected from a result of a texture analysis of the multispectral image of the retina of the particular subject, a result of a vessel morphology analysis of the multispectral image of the retina of the particular subject, and a combination thereof.

19. The system of claim 18, wherein the one or more secondary characteristics further include, for a particular subject, an element selected from an indication that a specific gene or group of genes is present or absent in a genotype of the particular subject, an age of the particular subject, a gender of the particular subject, a height of the particular subject, a weight of the particular subject, a list of medications prescribed to the particular subject, a blood pressure level of the particular subject, a cholesterol level of the particular subject, a blood glucose level of the particular subject, an image obtained by structural neuroimaging, a lifestyle factor, a body mass index, a set of administrative claims data, an assessment obtained for the particular subject from a cognitive test, and a combination thereof.

20. The system of claim 17, wherein the systemic disease having manifestations in the eyes of a subject is one of Alzheimer's disease, Parkinson's disease, multiple sclerosis, diabetes, vascular dementia, Lewis Body dementia, amyotrophic lateral sclerosis (ALS), and a cardiovascular disease.

* * * * *